US011007302B2

(12) United States Patent
Ruppert et al.

(10) Patent No.: US 11,007,302 B2
(45) Date of Patent: May 18, 2021

(54) AUTO-POLYMERIZABLE PROSTHETIC MATERIAL AND POLYMERIZED, FRACTURE-TOUGH PROSTHETIC MATERIAL WITH INCREASED COLOUR STABILITY

(71) Applicant: KULZER GMBH, Hanau (DE)

(72) Inventors: Klaus Ruppert, Maintal (DE); Alfred Hohmann, Schmitten (DE); Stephan Dekert, Wehrheim (DE)

(73) Assignee: KULZER GMBH, Hanau (DE)

( * ) Notice: Subject to any disclaimer, the term of this patent is extended or adjusted under 35 U.S.C. 154(b) by 238 days.

(21) Appl. No.: 15/323,121

(22) PCT Filed: Jun. 30, 2015

(86) PCT No.: PCT/EP2015/064866
§ 371 (c)(1),
(2) Date: Dec. 30, 2016

(87) PCT Pub. No.: WO2016/001236
PCT Pub. Date: Jan. 7, 2016

(65) Prior Publication Data
US 2017/0151368 A1   Jun. 1, 2017
US 2017/0340773 A9   Nov. 30, 2017

(30) Foreign Application Priority Data
Jul. 1, 2014   (DE) ............... 10 2014 109 234.1

(51) Int. Cl.
| | |
|---|---|
| A61L 27/26 | (2006.01) |
| A61L 27/18 | (2006.01) |
| A61L 27/16 | (2006.01) |
| A61L 27/48 | (2006.01) |
| A61L 27/50 | (2006.01) |
| A61K 6/893 | (2020.01) |

(52) U.S. Cl.
CPC ............. *A61L 27/26* (2013.01); *A61L 27/16* (2013.01); *A61L 27/18* (2013.01); *A61L 27/48* (2013.01); *A61L 27/50* (2013.01)

(58) Field of Classification Search
CPC .................................................. A61K 6/893
See application file for complete search history.

(56) References Cited

U.S. PATENT DOCUMENTS

| | | | |
|---|---|---|---|
| 5,502,087 A | 3/1996 | Tateosian et al. | |
| 5,554,665 A | 9/1996 | Tateosian et al. | |
| 6,653,375 B2 * | 11/2003 | Moszner | A61K 6/30 524/116 |
| 6,881,360 B2 * | 4/2005 | Stange | A61K 6/893 264/18 |
| 6,890,968 B2 * | 5/2005 | Angeletakis | A61K 6/76 523/115 |
| 7,091,258 B2 * | 8/2006 | Neubert | C02F 3/284 523/113 |
| 2005/0059751 A1 * | 3/2005 | Erdrich | A61K 6/887 523/113 |
| 2005/0124762 A1 * | 6/2005 | Cohen | A61K 6/0017 525/191 |
| 2006/0217488 A1 * | 9/2006 | Renz | A61K 6/083 525/70 |
| 2009/0192240 A1 | 7/2009 | Benz et al. | |
| 2011/0269894 A1 | 11/2011 | Miyamoto | |
| 2015/0038634 A1 * | 2/2015 | Sun | A61K 6/891 524/504 |

FOREIGN PATENT DOCUMENTS

| | | |
|---|---|---|
| DE | 694 26 093 T2 | 5/2001 |
| DE | 10 2005 012 825 A1 | 9/2006 |
| EP | 1 702 633 A2 | 9/2006 |
| WO | 2015/017556 A1 | 2/2015 |

OTHER PUBLICATIONS

Pac, 1991, 63, pp. 1227 (Manual on catalyst characterization (Recommendations 1991)).
Boverhof et al., "Comparative assessmentof nanomaterial definitions and safety evaluation considerations"; Regulatory Toxicology and Pharmacology 73, (2015) pp. 137-151.

* cited by examiner

*Primary Examiner* — Bethany P Barham
*Assistant Examiner* — Peter Anthopolos
(74) *Attorney, Agent, or Firm* — Norris McLaughlin, P.A.

(57) ABSTRACT

The subject matter of the invention is an autopolymerisable two-component prosthetic base material and a method for its production comprising A) at least one liquid monomer component, and B) at least one powdered component, whereby the prosthetic material comprises in components (A) and/or (B) (i) at least one initiator or one initiator system for autopolymerisation, (ii) core-shell particles modified by an elastic phase, and (iii) at least one urethane (meth) acrylate.

21 Claims, 1 Drawing Sheet

AUTO-POLYMERIZABLE PROSTHETIC MATERIAL AND POLYMERIZED, FRACTURE-TOUGH PROSTHETIC MATERIAL WITH INCREASED COLOUR STABILITY

This application is a 371 of PCT/EP2015/064866, filed Jun. 30, 2015, which claims foreign priority benefit under 35 U.S.C. § 119 of German Patent Application No. 10 2014 109 234.1, filed Jul. 1, 2014, the disclosures of which are incorporated herein by reference.

Subject matter of the invention is an autopolymerisable two-component prosthetic base material and a method for its production comprising (A) at least one liquid monomer component, and (B) at least one powdered component, whereby the prosthetic material comprises in components (A) and/or (B), (i) at least one initiator or one initiator system for autopolymerisation, (ii) core-shell particles modified by an elastic phase, and (iii) at least one urethane (meth)acrylate, in particular urethane dimethacrylate.

Prosthetic materials tend to chip in thin regions upon removal from the investment material (plaster). Moreover, due to the limited motor skills of prosthesis wearers, who are usually more advanced in age, prostheses occasionally are dropped onto a hard surface (tiles, washbasin), which may also cause them to chip, or to break. Said chipping is associated with additional work and additional costs for the dental laboratory and is therefore undesirable. Moreover, in particular in the event of implant-supported dental prostheses, appreciably higher chewing forces may cause the prosthesis to be damaged.

For these reasons, there is a need to have a prosthesis material that tolerates brief loads, such as the afore-mentioned, brief high mechanical loads, without the material being damaged. These prosthesis materials are referred to as so-called high-impact materials. Requirements for said materials are described in DIN ISO 20795-1. Products meeting these requirements have been on the market for some time, but are all members of the group of hot-curing prosthesis materials.

Up to now, only two products are known as cold-curing polymers. Both products are either very elaborate to process (Ivobase High Impact/Fa. Ivoclar Vivadent: special application device, special cuvettes, special investment material, closed system) or show aesthetically unsatisfactory color changes due to the added additives.

It was an object of the invention to provide a material, in particular a material suitable in the medical field, preferably a prosthesis material, for cold-polymerisation, which exceeds the requirements concerning fracture toughness of norm DIN ISO 20795-1. Moreover, it was the object for the material to be produced without elaborate additional devices, in particular, processing without special additional devices shall also be possible, and the material shall only be processed by typical dental technology techniques and devices. It was another object to provide a highly fracture-tough material, in particular a prosthesis material whose transparency is not affected compared with the basic material.

It has surprisingly been found, that a material, in particular a prosthesis material/base material, having the required properties concerning fracture toughness and, preferably, concerning the requirements for transparency, can be provided by adding core-shell particles and urethane (meth) acrylate to a prosthetic base material.

In principle, the following technologies have been considered in order to attain high fracture toughness, core-shell particles or special elastifying liquid additives, such as, for example, butadiene copolymers, butadiene-acrylonitrile copolymers, silicone acrylates, or urethane acrylates. Up to now, core-shell particles have been unsuitable for cold-curing polymers, since the swelling time, being appreciably shorter compared with hot-curing polymers, was insufficient for swelling of the core-shell particles.

The afore-mentioned liquid additives, such as, for example, acrylonitrile-butadiene copolymer, tended to show yellowing of the prosthesis material. This is typically done in the presence of oxidizing substances, such as, for example, peroxides or atmospheric oxygen. Moreover, the liquid additives, such as, for example, silicone acrylates, have a refractive index markedly different from PMMA and thus typically result in forming an opaque material. The urethane acrylate-based liquid additives, such as, for example, urethane acrylate, often lead to an improvement of the fracture toughness of materials, but do not meet the minimum requirements concerning fracture toughness of ISO 20795-1. Another disadvantage of some additives results in water absorption during the polymerisation process resulting in an undesired whitening of the prosthesis material while worn.

According to the invention, the object is met by synergistical use of core-shell particles and at least one urethane methacrylate in the prosthetic base material. Combining core-shell particles in the liquid monomer component in conjunction with at least one urethane acrylate or one urethane methacrylate in the liquid can achieve particularly good results in the polymerised prosthesis material. The selection of specific core-shell particles having a refractive index similar to that of the polymerised prosthetic material ensured high transparency of the prosthesis material. The core-shell particles therefore preferably have a refractive index of about 1.49 (R.I.~1.4900).

Particularly preferred core-shell particles according to the invention are present in aggregated form. The objects can be met by use of aggregated core-shell particles (irregularly shaped aggregates, $d_{50}$~50-300 µm), the primary particle size is approximately 200-400 nm. Probably, the core-shell particles are present in aggregated form due to surface interaction in the solid. The additive is mixed with the liquid and forms a stable suspension that just weakly sediments within a few weeks. As a result of suspending in MMA, the aggregates relatively quickly degrade into the primary particles.

By inventive use of the core-shell particles as a high-impact additive in conjunction with at least one urethane acrylate, preferably a urethane methacrylate, it is possible to produce prosthesis materials meeting the requirements concerning high-impact properties of ISO 20795-1. Moreover, a prosthesis material having its flexural strength and E-modulus in the same order as non-high-impact materials and, at the same time, being highly transparent and colour-stable, can be provided. The prostheses according to the invention do not show any whitening by contact with water-containing materials, such as, for example, duplicating gels or plasters, during and after polymerisation process.

Moreover, the prosthesis material according to the invention can be mixed and processed using usual dental technology methods and instruments. Conventional techniques and means common to the dental technician can be used for processing. Special investment materials, plasters, cuvettes, devices etc. (such as, e.g., in the Ivoclar-system) can be avoided.

In order to distinguish prosthetic materials from usual dental materials, it is emphasized that prosthetic materials comprise substantial amounts of polymeric powdered components, such as PMMA (Poly(meth)methylacrylate) and/or (Poly(ethyl)methacrylate), in particular of greater than or equal to 50% by weight in the total composition. Usual prosthetic materials are usually provided in a kit having a powdered component and a liquid component. Dental materials for the production of fillings are largely based on polymerisable monomers preferably being present in an amount of greater than 55% by weight in the polymerisable composition.

According to the invention, core-shell particles, possibly being present as aggregates, whereby, however, said aggregates can be separated into single particles during the short swelling time, in particular degrade into single particles after adding the liquid monomer component, are particularly well-suited for use.

The subject matter of the invention is an autopolymerisable and/or cold-polymerisable two-component prosthetic base material, in particular a polymerisable prosthetic material, comprising
A) at least one liquid monomer component,
B) at least one powdered component,
whereby the prosthetic material comprises in components (A) and/or (B) (i) at least one initiator or one initiator system for autopolymerisation or cold-polymerisation, (ii) core-shell particles modified by an elastic phase, and (iii) at least one urethane (meth)acrylate, in particular one urethane dimethacrylate, preferably one bis(methacryloxy-2-ethoxycarbonylamino)alkylene, Diurethane acrylate oligomer, alkyl-functional urethane dimethacrylate oligomers, aromatically functionalised urethane dimethacrylate oligomers, aliphatic unsaturated urethane acrylates, bis(methacryloxy-2-ethoxycarbonylamino)-substituted polyether, aromatic urethane diacrylate oligomers, aliphatic urethane diacrylate oligomers, mono-functional urethane acrylates, aliphatic urethane diacrylates, hexa-functional aliphatic urethane resins, aliphatic urethane triacrylates, UDMA, aliphatic urethane acrylate oligomers, unsaturated aliphatic urethane acrylate.

As explained below, the components of the initiator system may be divided between components A) and B).

The prosthetic material according to the invention, as being polymerised prosthetic material, preferably has a fracture toughness ($k_{max}$; maximum stress intensity factor) of greater than or equal to 1.9 MPa·m$^{1/2}$, in particular of greater than or equal to 2 MPa·m$^{1/2}$, and, preferably at the same time, a total fracture work ($W_f$) of greater than or equal to 900 J/m$^2$. Particularly preferably, the fracture toughness is greater than or equal to ($\geq$) 2.1 MPa·m$^{1/2}$, preferably $\geq$2.3 MPa·m$^{1/2}$, $\geq$MPa·m$^{1/2}$. Furthermore, it is preferred for the fracture work to be, at the same time, greater than $\geq$900 J/m$^2$, in particular greater than $\geq$950 J/m$^2$, 1000 J/m$^2$, particularly preferably greater than or equal to 1030 J/m$^2$. Particularly preferably, the flexural strength is, in addition, greater than 65 MPa, particularly preferably greater than 70 MPa, more preferably greater than 75 Mpa. A particularly preferred prosthetic material has a fracture toughness of >2.3 MPa·m$^{1/2}$ and a total fracture work of >1000 J/m$^2$.

Furthermore, it is preferred that the transparency of the unpigmented, polymerised protheses is in the range of greater than or equal to 85%, in particular of greater than or equal to 90% (measured against plates having a thickness of 3 mm).

Particularly preferably, component (A) comprises at least one liquid monomer component, (i) at least one initiator or one initiator system for autopolymerisation or one part of the components of the initiator system, (ii) core-shell particles modified by at least one elastic phase, and (iii) at least one urethane (meth)acrylate, in particular urethane dimethacrylate.

In this context, it is particularly preferred for component (ii) core-shell particles modified by at least one elastic phase to be present at 0.001 to 20% by weight, in particular up to 10% by weight, preferably up to 5% by weight, based on the total composition of component (A), and for (iii) at least one urethane (meth)acrylate, in particular one urethane dimethacrylate, to be present at 0.001 to 20% by weight, in particular up to 10% by weight, more preferably up to 5% by weight, based on the total composition of component (A) (i.e. on 100% by weight of component (A)).

Despite the added high-impact modifier (core-shell particles and urethane (meth)acrylate) the prosthetic base material according to the invention does not show negative influence on Suntest according to ISO 20795-1.

The core-shell particles are also referred to as high-impact modifier.

Particularly preferred prosthetic base materials preferably have core-shell particles, in which the distribution of the elastic phase of the modified core-shell particles is selected from possibilities a to d: a) elastic phase as core (e.g. made of butylacrylate) in solid outer shell (e.g. made of PMMA) (core-shell particles; b) multiple elastic phases as cores in a solid matrix; c) core-shell particles from a), distributed in solid matrix, and d) solid core with elastic phase as outer shell.

Core-shell particles according to the invention can also have the following multi-layer structure, e) an inlying core with multiple layers as shells and one outer shell, whereby, in particular, (i) at least one of the shells, in particular the outer shell, is solid and the remaining shells and the core, each independently, consists of elastic phases. In alternatives, the elastic phases and the solid phases may be otherwise divided between the shells and the core.

Furthermore, preferred core-shell particles have a refractive index similar to that of the polymerised prosthesis material. Preferably, the refractive index of the core-shell particles is about 1.4900 having a total variability of the present value of plus/minus 0.02, in particular +/−0.01. According to the invention, particularly preferred core-shell particles are present in aggregated form. In this context, the aggregates of the core-shell particles, which can be randomly shaped, as being an irregularly shaped aggregate, have an average diameter of $d_{50}$~50-300 µm. The preferred size of the primary particle size is less than 500 nm, in particular up to 100 nm, preferably from 200-400 nm. Core-shell particles having a primary particle size of less than or equal to 200 nm to 2 nm, such as between 150 to 10 nm, can also be used as core-shell particles.

Preferably, the core-shell particles have a refractive index of 1.48 to 1.60, in particular of 1.49 to 1.55. Particularly preferably, the refractive index of the core-shell particles is in the range of the refractive index of PMMA, PEMA, preferably, the refractive index is therefore about 1.48 to 1.50.

Core-shell particles whose density is 0.9 to 1.5 g/ml, in particular 0.95 to 1.4 g/ml are also preferred. Preferably, the bulk density is, at the same time, 0.1 to 0.6 g/ml, preferably 0.1 to 0.6 g/ml.

A solid outer shell, solid matrix, solid core shall be understood to mean a material, which preferably has a lower elasticity than the material of the elastic phase. Preferably, the elasticity of the solid materials is at least 40% less than that of the elastic phase. Preferred inorganic solid cores show substantially no deformation under the influence of a force, while the organic solid materials undergo an appreciably lower deformation under the influence of a force than the elastic phase. The solid materials as being a solid outer shell, solid matrix and/or solid core stabilize the elastic phase in its shape. An elastic phase is formed by at least one elastic material, which undergoes a reversible deformation under the influence of a force. The deformation of the elastic phase advantageously is fully reversible without force effect.

Preferred components B) preferably comprise at least one powdered component comprising a) polymeric particles comprising polymers in the form of polymer powder comprising polyalkyl(meth)acrylates, optionally being crosslinked and being present as homopolymer or copolymer, whereby the polymers are based on at least one monomer comprising a (meth)acrylat group, selected from methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, a mixture comprising at least one of said (meth)acrylates and/or copolymers comprising one or at least two of the afore-mentioned monomers, polyamide particles, polyamide fibers. Furthermore, the polymeric particles can also comprise mixtures of dental monomers, such as, for example, MMA, and, additionally, at least one crosslinker.

Particularly preferably, the powdered component comprises polymethylmethacrylate (PMMA) beads as polymeric particles and/or splitter polymers, in particular having particle sizes of 10-100 µm, and/or is based on copolymers comprising as comonomers, being polymerised into the copolymer, styrene, alpha-methylstyrene, vinyltoluene, substituted vinyltoluene, such as vinylbenzylchloride, vinylhalogenide, such as vinylchloride, vinylester, such as vinylacetate, heterocyclic vinyl compounds, such as 2-vinylpyridine, vinylpropionate, butadiene, isobutylene, 2-chlorobutadiene, 2-methylbutadiene, vinylpyridine, cyclopentene, (meth)acrylic acid ester, such as methylmethacrylate, ethylmethacrylate, butylmethacrylate, butylacrylate and hydroxyethylmethycrylate, moreover acrylonitrile, maleic acid and maleic acid derivatives, such as, for example, maleic acid anhydride, fumaric acid and fumaric acid derivatives, such as fumaric acid esters, acrylic acid, methacrylic acid, as well as acryl(meth)acrylates, such as benzylmethacrylate or phenylmethacrylate, as well as, optionally, mixtures of said comonomers, and, optionally additionally, b) inorganic fillers comprising pyrogenic or precipitated silicas, dental glasses, such as aluminosilicate glasses or fluoroaluminosilicate glasses, bariumaluminium silicate, strontium silicate, strontium borosilicate, lithium silicate, lithiumaluminium silicate, phyllosilicates, zeolites, amorphous spherical fillers based on oxide or mixed oxide, in particular mixed oxides of $SiO_2$ and $ZrO_2$, glass fibers and/or carbon fibers, as well as mixtures comprising said powdered components a) and b).

The b) inorganic fillers are usually used in amounts of 0 to 10% by weight, preferably of 0.0001 to 3% by weight, based on the total prosthetic plastic composition and/or the sum of components (A) and (B). In component (B) they are usually present in the range of 0 to 20% by weight, preferably of 0.001 to 10% by weight, based on the total composition of component (B) of 100% by weight.

Polymeric particles, which are based on at least one (meth)acrylate monomer having just one (meth)acrylate group or which are based on a mixture of at least two of said (meth)acrylate monomers are also in the scope of the invention.

Core-shell particles according to the invention preferably comprise as elastic phase at least one poly-(n-butyl acrylate) PBA, butadiene-styrene copolymer, nitrile-butadiene copolymer, silicon rubber—(graft copolymers), polyurethane polymer, polyolefin-based polyurethane (polybutadiene-based polyurethane), which can preferably be present in MMA. The particle size of the core-shell particles can be less than or equal to 500 nm, such as between 50 nm to 500 nm, in particular less than or equal to 400 nm to 100 nm, or, alternatively, less than 100 nm to 2 nm, the elastic phase can also be based on polydimethylsiloxane-modified polyurethanes and/or epoxy-functionalised elastic phases.

Core-shell particles according to the invention comprise as solid shell, solid core and/or solid matrix at least one (meth)acrylate polymer, preferably one alkyl(meth)acrylate polymer, such as PMMA, polystyrene, an epoxy-functionalised core, as well as homo- or co-condensates of the afore-mentioned polymers.

Particularly preferred core-shell particles, in conjunction with urethane (meth)acrylate, provide the polymerised prosthetic material with high impact properties, with a fracture toughness of $\geq 1.9$ MPa·m$^{1/2}$, preferably MPa·m$^{1/2}$, and a fracture work of $\geq 900$ J/m$^2$. Preferred core-shell particles comprise aggregates having $d_{50}<400$ µm and primary particle sizes of $d_{50}$ less than 500 nm. More preferably, the primary particles of the core-shell particles can be greater than or equal to 100 nm, in particular as a $d_{50}$-value.

Core-shell particles comprising an elastic core comprising acrylate polymers with solid outer shell, in particular having a particle size of less than 1 micrometer, are also suitable. More preferably, the core-shell particles have groups reactive against polymerisable monomers, preferably, the outer shell is functionalised by (meth)acrylate groups. Alternative core-shell particles comprise as solid core a silicon dioxide and an elastic shell comprising at least one nitrile-butadiene copolymer. Further core-shell particles may be present in a monomer liquid.

According to the invention, di-functional and multi-functional urethane (meth)acrylates, such as, in particular, urethane di(meth)acrylate, are preferably suitable as urethane (meth)acrylate, particularly preferably, the at least one (iii) urethane dimethacrylate (UDMA) is selected from linear alkyl- or branched alkyl-functionalised urethane dimethacrylates, urethane dimethacrylate-functionalised polyethers, in particular bis(methacryloxy-2-ethoxycarbonylamino) alkylene, bis(methacryloxy-2-ethoxycarbonylamino)-substituted polyether, preferably 1,6-bis(methacryloxy-2-ethyxycarbonylamino)-2,4,4-trimethylhexane.

Suitable urethane (meth)acrylates are available under the following brand names: Ebecryl 230 (aliphatic urethane diacrylate), Actilane 9290, Craynor 9200 (Diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (monofunctional urethane acrylate), Photomer 6210 (cas no. 52404-33-8, aliphatic urethane diacrylate), Photomer 6623 (hexa-functional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate).

Furthermore, a subject matter of the invention is a prosthetic base material comprising a (A) liquid monomer component, which comprises at least one monomer, in particular a mixture of monomers from a) methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, benzyl-, furfuryl- or phenyl(meth)acrylate, a mixture comprising at least one of said (meth)acrylates and/or copolymers comprising one or at least two of the afore-mentioned monomers, and/or b) two- and/or multi-crosslinkers (>2) comprising 1,4-butandiol dimethacrylate (1,4-BDMA) or pentaerythritol tetraacrylate, bis-GMA monomer (bisphenol-A-glycidylmethacrylate), triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra (meth)acrylate, as well as butanediol di(meth)acrylate, ethylene glycol di(meth)acrylate, polyethylene glycol di(meth) acrylate, ethoxylated/propoxylated bisphenol-A-di(meth) acrylate, a mixture comprising at least one of said (meth) acrylates and/or copolymers comprising one or at least two of the afore-mentioned monomers.

Suitable alkylmethacrylates for liquid component (A) are methyl-, ethyl-, n-propyl-, i-propyl-, n-butyl-, t-butyl-, i-butyl-, benzyl- and furfurylmethacrylate or mixtures thereof. Of these, methylmethacrylate is particularly preferred.

Preferably, the (A) liquid monomer component comprises
a.1) >85% by weight of at least one mono-functional (meth) acrylate-functional monomer component, in particular 85 to 90% by weight,
a.2) 0-15% by weight of at least one difunctional di(meth) acrylate-functional monomer component, in particular 0.01 to 15% by weight, 1 to 10% by weight, and
a.3) 0-10% by weight of at least one (meth)acrylate-functional tri-functional (meth)acrylate or one multi-functional (meth)acrylate, in particular 0.01 to 10% by weight, preferably 1.0 to 8% by weight,
b) 0-5% by weight of stabilizers and activators, initiators, in particular 0.01 to 5% by weight, preferably 0.1 to 3% by weight,
c) from 0.001 to 20% by weight urethane (meth)acrylate, in particular 0.01 to 10% by weight, preferably from 0.5 to 5% by weight, particularly preferably from 0.01 to 3% by weight,
d) from 0.001 to 20% by weight core-shell particles, in particular 0.001 to 10% by weight, preferably 1 to 10% by weight, particularly preferably 0.001 to 5% by weight, preferably between 0.5 to 5% by weight, whereby the total composition of liquid monomer component A) totals 100% by weight. The total composition of all components of the powdered component (B) totals 100% by weight, as well. The core-shell particles are usually suspended in the monomers.

According to the invention, the total composition of the powdered component (B) is composed as follows:
b.1) from 100% by weight of polymeric particles and, optionally, inorganic fillers or a mixture thereof, the content can preferably be composed as follows: from 100 to 80% by weight polymeric particles, such as PMMA, PEMA, from 0 to 20% by weight inorganic fillers, such as dental glasses, metal oxide basis or mixed oxide basis ($SiO_2$, $ZrO_2$ and/or $TiO_2$), in particular 0.01 to 10% by weight,
b.2) 0-5% by weight of at least a part of an initiator system, in particular 0.01 to 4% by weight, and
b.3) 0-5% by weight of pigments, excipients, stabilizers, or mixtures comprising at least one of the afore-mentioned components, in particular 0.01 to 4% by weight, the afore-mentioned total composition of the powdered component totals 100% by weight.

Preferably, powdered polymeric components, such as PMMA, of different particle sizes can possibly be used, as homo- and/or copolymers: a) homopolymer bead 1 ($d_{50}$~40-50 μm) and b) bead 2 ($d_{50}$~55-70 μm), and, optionally, copolymer c) bead 3 ($d_{50}$~40-50 μm).

The total composition (A) with 100% by weight and the total composition (B) with 100% by weight are being mixed at a weight ration of (A) to (B) of 1 to 20 to 20 to 1, preferably at a weight ratio of (A) to (B) of 5 to 15 to 9 to 8, preferably of 5 to 8 to 8 to 12, preferably at a weight ratio of (A) to (B) of 7 to 10, in particular having a total variability of the present value of plus/minus 1, preferably of 0.5.

The monomers that are common in the field of dentistry are conceivable as further liquid monomers: Examples include radically polymerisable mono-functional monomers, such as mono(meth)acrylate, methyl-, ethyl-, butyl-, benzyl-, furfuryl- or phenyl(meth)acrylate.

Typical di-functional monomers, also referred to as cross-linker and/or multi-crosslinker, include BDMA 1,4-butandiol dimethacrylate (1,4-BDMA), bis-GMA monomer (bisphenol-A-glycidylmethacrylate) (an addition product of methacrylic acid an bisphenol-A diglycidylether), diethylene glycol dimethacrylate, bisphenol-A di(meth)acrylate, decanediol di(meth)acrylate, dodecandiol di(meth)acrylate, hexyldexandiol di(meth)acrylate, as well as butanediol di(meth)acrylate, ethylene glycol di(meth)acrylate, polyethylene glycol di(meth)acrylate, ethoxylated/propoxylated bisphenol-A-di(meth)acrylate. The following di-functional monomers may also be added as diluting agent (low viscosity acrylates, such as triethylene glycol dimethacrylate (TEGDMA) and diethylene glycol dimethacrylate (DEGMA)). Tri- and tetra-functional monomers and/or multi-crosslinker comprise trimethylolpropane tri(meth)acrylate, tris(2-hydroxyethyl)-isocyanurate triacrylate, pentaerythritol tetraacrylate. In the following, further crosslinkers are also disclosed among the polymeric particles comprising copolymers that comprise at least one (meth)acrylate monomer having two, three, four, five or six (meth)acrylate groups.

The amount of aliphatic (meth)acrylate being liquid at room temperature in the mixed, not yet polymerised prosthetic base material according to the invention, in particular comprising components (A) and (B), is, for example, 0.5% to 40% by weight, preferably 20 to 40% by weight. The aliphatic (meth)acrylate can be present either in the liquid monomer component (A) or, optionally, at least in parts in the solid component and/or powder component (B) or in both. Preferably, it is present in component (A).

Furthermore, a subject matter of the invention is a prosthetic base material that, preferably additionally, comprises in component (A), (B) or in (A) and (B) at least one or more substance(s) from the group consisting of fillers, pigments, stabilizers, regulators, antimicrobial additives, UV-absorbing agents, thixotroping agents, catalysts and crosslinkers. Rather small amounts of said additives—as of pigments, stabilizers and regulators—are used, for example, a total of 0.01 to 3.0, in particular 0.01 to 1.0% by weight, based on the total mass of the material. Suitable stabilizers include, for example, hydroquinone monomethylether or 2,6-di-tert.-butyl-4-methylphenol (BHT).

Another subject matter of the invention is a prosthetic base material that optionally additionally has at least one initiator or at least one initiator system for autopolymerisation, which are present in the liquid component (A), the powdered component (B) or in (A) and (B) depending on the reaction conditions and/or the polymerisation system.

The following initiators and/or initiator systems for auto- or cold-polymerisation comprise a) at least one initiator, in particular at least one peroxide and/or azo compound, in particular LPO: dilauroylperoxide, BPO: dibenzoylperoxide, t-BPEH: tert-butylper-2-ehtylhexanoate, AIBN: 2,2"-azobis-(isbutyronitrile), DTBP: di-tert-butylperoxide, and, optionally, b) at least one activator, in particular at least one aromatic amine, such as N,N-dimethyl-p-toluidine, N,N dihydroxyethyl-p-toluidine and/or p-dimethylamino-benzoic acid diethylester, or c) at least one initiator system selected from redox systems, in particular a combination selected from dibenzoylperoxide, dilauroylperoxide, and camphorquinone with amines selected from N,N dimethyl-p-toluidine, N,N-dihydroxyethyl-p-toluidine, and p-dimethylamino-benzoic acid diethylester, or a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or one copper complex, and (iii) at least one compound having an ionic halogen atom, particularly preferred is a redox system comprising 1-benzyl-5-phenyl barbituric acid, copper acetylacetonate and benzyldibutylammoniumchloride. Particularly preferably, the polymerisation in the two-component prosthetic base material is started by a barbituric acid derivative.

The invention also relates to a method for the production of a polymerised prosthetic base material, as well as a prosthetic material obtainable by the method, in which the components A) at least one liquid monomer component, and B) at least one powdered component are mixed and subsequently polymerised and/or cured.

Particularly preferably, A) the liquid monomer component comprises methylmethacrylate, butanediol methacrylate and, optionally, at least one methacrylate-based di-, tri- and/or tetra-functional monomer as multi-crosslinker, such as, for example, tris(2-hydroxyethyl)-isocyanurate triacrylate and/or pentaerythritol tetraacrylate, as well as one urethane diacrylate, at least a part of an initiator system, and B) comprises PMMA beads, barbituric acid or a barbituric acid derivative, as well as, optionally, pigments. To produce the prosthetic base material, components A) and B) are mixed.

According to a preferred variant of the method the A) monomer component and the B) powdered component are being mixed at a weight ratio of 1:50 to 50:1, in particular at a weight ratio of 7:10 (10 g powder, 7 ml liquid, having similar density), in particular with a total variability of the present value of plus/minus 1, preferably plus/minus 0.5.

The mixing of components A) and B) can be carried out according to the invention by means of simple measures known to the dental technician, such as by means of a spatula.

Another subject matter of the invention is a pigmented, polymerised prosthetic base material. Furthermore, a subject matter of the invention is an unpigmented, polymerised prosthetic base material having a transparency of greater than or equal to 85% (measured against 3 mm plates).

According to a further embodiment, a subject matter of the invention is the use of core-shell particles modified by at least one elastic phase and at least one urethane di(meth) acrylate or one derivative of an urethane di(meth)acrylate in auto- or cold-polymerisable prosthetic materials.

Another subject matter of the invention is the use of the prosthetic material in the human dental field in particular for dental prostheses, parts of prostheses, for manufacture of occlusal splints, of surgical guides for implantology, of mouthguards, as bone cement, as bone cement for cementing of artificial articular protheses, crowns, telescopic prostheses and telescopic crowns, veneers, dental bridges, prosthetic teeth, implants, implant parts, abutments, superstructures, orthodontic appliances and instruments, in veterinary field, in particular for hoof repair materials, as bone cement, as bone cement for cementing of artificial articular protheses, orthodontic appliances and instruments.

According to a further alternative, a subject matter of the invention is a Kit comprising an autopolymerisable prosthetic material, whereby the Kit comprises separated components (A) and (B).

Auto- or cold-polymerisable according to the invention shall be understood to mean a prosthetic material meeting the criteria according to ISO 20795-1 (Pt. 3.1). Cold-polymerising plastic materials shall be understood to mean compositions, which polymerise below 65° C. Preferably, cold-polymerising prosthetic materials according to the invention can independently cure and/or polymerise in a temperature range from 50° C. to 65° C., preferably from 50° C. to 60° C., more preferably from 50° C. to 55° C., after mixing components (A) and (B). According to the aforementioned norm, polymerisable compositions, which independently cure and/or polymerise above 65° C., are referred to as heat-curing compositions.

The powder component of two-component prosthetic base material usually comprises a polymer powder, in particular based on methacrylate, and/or a bead polymer based on methacrylate. In this field, beat polymers are often referred to as powder.

Bead polymers, in particular those made of (meth)acrylates, are known to the person skilled in the art. Bead polymers based on polyalkyl(meth)acrylates are obtained in known manner through precipitation polymerisation or suspension polymerisation. In this context, suspension polymerisation usually yields larger particles. The average particle sizes vary over a wide range and can be, for example, from 0.1 µm to 250 µm. Cross-linking bead polymers are conceivable as well. Suitable multi-functional cross-linker molecules are evident from the listing of common monomers that are common in dentistry provided above.

Further comonomers can also be polymerised into the bead polymers, as explained above.

In a preferred embodiment, crosslinkers have been polymerised, at least in part, into the beads of the first (co)polymer and/or into the beads of the second (co)polymer. Accordingly, the first and second bead polymers also comprise cross-linked and partly cross-linked bead polymers.

For cross-linking, it is common to resort to multi-functional comonomers or multi-functional oligomers. Aside from di-, tri- and poly-functional (meth)acrylates, graft crosslinkers having at least two different reactive C—C double bonds, for example, alkylmethacrylates and alkylacrylates, as well as aromatic crosslinkers, such as 1,2-divinylbenzene, 1,3-divinylbenzene, and 1,4-divinylbenzene, are suitable for this purpose. Amongst the difunctional (meth)acrylates, in particular, the (meth)acrylates of propandiol, butanediol, hexandiol, octandiol, nonandiol, decanediol, and eicosandiol, as well as the di(meth)acrylates of ethylene glycol, triethylene glycol, tetraethylene glycol, dodecaethylene glycol, tetradecanethylene glycol, propylene glycol, dipropylene glycol, and tetradecanpropylene glycol, moreover glycerol di(meth)acrylate, 2,2-bis[(gamma-methacryloxy-beta-oxypropoxy)-phenyl propane], bis-G MA, bisphenol-A di methacrylate, neopentylglycol di(meth)acrylate, 2,2-(di-methacryloxypolyethoxy-phenyl) propane with 2 to 10 ethoxy groups per molecule, as well as 1,2-bis(3-methacryloxy-2-hydroxypropoxy)butane, shall be mentioned. Exemplary, multi-functional (meth)acrylates include, for example, di-, tri- and/or tetra(meth)acrylates, such as 1,4-butanediol dimethacrylate, ethylene glycol dimethacrylate, as well as di- or trivinylic compounds, such as divinylbenzene.

The content of said crosslinker molecules in the starting mixture of the bead polymer is in the range from 0.1% by weight to 10% by weight, in particular in the range from 0.5% by weight to 5% by weight.

In an expedient embodiment, at least one crosslinker is present in liquid component (A) aside from at least one of the afore-mentioned mono-functional alkylmethacrylate monomers. This can be, for example, multi-functional monomers, comonomers or multi-functional oligomers. Aside from di-, tri- and poly-functional (meth)acrylates, graft crosslinkers having at least two different reactive C—C double bonds, for example, alkylmethacrylates and alkylacrylates, as well as aromatic crosslinkers, such as 1,2-divinylbenzene, 1,3-divinylbenzene and 1,4-divinylbenzene, are suitable for this purpose. Amongst the difunctional (meth)acrylates, in particular, the (meth)acrylates of propandiol, butanediol, hexandiol, octandiol, nonandiol, decanediol, and eicosandiol, as well as the di(meth)acrylates of ethylene glycol, triethylene glycol, tetraethylene glycol, dodecaethylene glycol, tetradecanethylene glycol, propylene glycol, dipropylene glycol, and tetradecanpropylene glycol, moreover glycerol di(meth)acrylate, 2,2-bis[(gamma-methacryloxy-beta-oxypropoxy)-phenyl propane], bis-G MA, bisphenol-A di methacrylate, neopentylglycol di(meth)acrylate, 2,2-(di-methacryloxypolyethoxy-phenyl) propane with 2 to 10 ethoxy groups per molecule, as well as 1,2-bis(3-methacryloxy-2-hydroxypropoxy)butane, shall be mentioned. Exemplary, multi-functional (meth)acrylates include, for example, di-, tri- and/or tetra(meth)acrylates, such as 1,4-butanediol dimethacrylate, ethylene glycol dimethacrylate, as well as di- or trivinylic compounds, such as divinylbenzene. It is self-evident that mixtures of said crosslinker molecules can be used as well. Such multi-functional compounds, in particular di- and/or tri-functional compounds, that possess elastic elements and are therefore suitable for imparting flexible properties on prosthetic materials that are obtained from prosthetic starting materials, are particularly suitable as well.

Exemplary, Dimethacrylates, such as 1,4-butanediol dimethacrylate, are to be mentioned. Said crosslinker molecules can be present in liquid component (A) in amounts in the range from 0.1 to 20% by weight, preferably in the range from 1 to 10% by weight, for example, 5% by weight.

In another embodiment, liquid component (A) may contain further comonomers aside from, for example, methylmethacrylate as the preferred main monomer (>50% by weight).

The radical initiator system required for polymerisation is contained in liquid component (A) and/or powdered component (B) depending on reaction conditions and/or polymerisation system. Pertinent details are known to the person skilled in the art. For example, in base mixtures for cold-cure polymers, the initiator system is most often present in both components, the liquid component and the powdered component, and is thus combined when mixing said components. Accordingly, one initiator component (c) is usually present in powdered component (B), in particular in the form of peroxides, perketals, peresters and/or azo compounds. Another part of the initiator system (c), usually a co-initiator, can be present in liquid component (A). It is also feasible to use as initiators residual contents of initiator components that did not react during production of the powdered components, for example, peroxides, such as dibenzoylperoxide.

In principle, suitable initiators for the polymerisation reaction of cold and/or auto-polymerising starting mixtures are basically those that can be used to initiate radical polymerisation reactions. Preferred initiators are peroxides, as well as azo compounds, such as, for example, the following: LPO: dilauroylperoxide, BPO: dibenzoylperoxide, t-BPEH: tert-butylper-2-ethylhexanoat, AIBN: 2,2"-azobis-(isobutylnitrile), DTBP: di-tert-butylperoxide.

Suitable activators, for example, aromatic amines, can be added to accelerate the radical polymerisation through peroxides. Exemplary, N,N-dimethyl-p-toluidine, N,N-dihydroxyethyl-p-toluidine, and p-dibenzylamino-benzoic acid diethylester are to be mentioned as suitable amines. In this context, the amines usually function as co-initiators and are usually present in an amount of up to 0.5% by weight.

The afore-mentioned redox systems are suitable as radical initiator systems. In an expedient embodiment, a redox system of this type comprises barbituric acid or thiobarbituric acid, or a barbituric acid or thiobarbituric acid derivative (for example 25 to 80% by weight), at least one copper salt or copper complex (for example 0.1 to 8% by weight), and at least one compound having an ionogenic halogen atom (for example 0.05 to 7% by weight). Exemplary, suitable ingredients of the afore-mentioned redox system are 1-benzyl-5-phenylbarbituric acid, copper acetylacetonate, and benzyldibutylammoniumchloride.

Curing of the compositions preferably proceeds through redox-induced radical polymerisation at room temperature and/or at slightly elevated temperature and under a slight pressure in order to avoid the formation of bubbles. Examples of suitable initiators for polymerisation performed at room temperature include redox initiator combinations, such as, for example combinations of benzoyl- or laurylperoxide with N,N-dimethyl-sym-xylidine or N,N-dimethyl-p-toluidine. A particularly preferred initiator system consists of a combination of barbituric acid in conjunction with copper and chloride ions, as well as above-mentioned peroxides. Said system is characterised by its high level of colour-stability.

Furthermore, the powdered component (B) and/or the liquid component (A) can be provided in known manner with further additives from the group of stabilizers, UV-absorbing agents, thixotroping agents and fillers.

BRIEF DESCRIPTION OF THE DRAWINGS

The subject matter of the invention is illustrated in more detail by FIGS. 1a to d, without meaning to thus limit the invention to these embodiments.

EXAMPLES

Figure 1D:
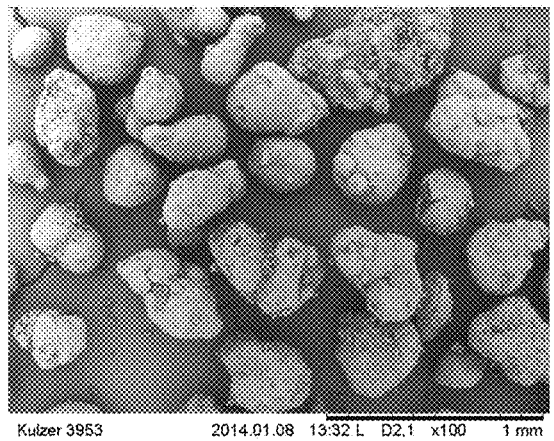
FIG. 1a and FIG. 1b: SEM—images of the core-shell particles (left: 100×, right: 10,000×)
FIGS. 1c and d: SEM-image of the additive being suspended in MMA and dried prior to the image (left: 500×, right: 10,000×)
Figure 1D:
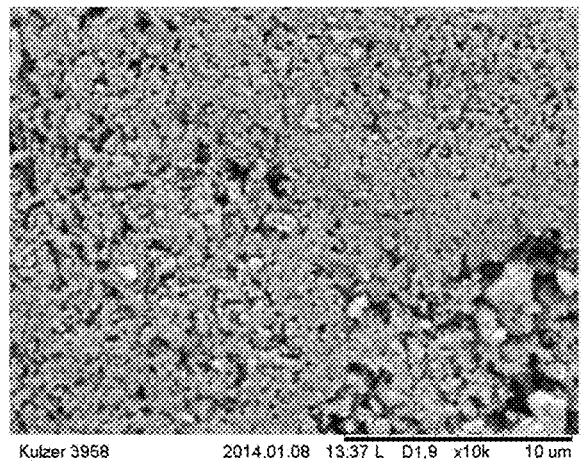
Figure 1D:
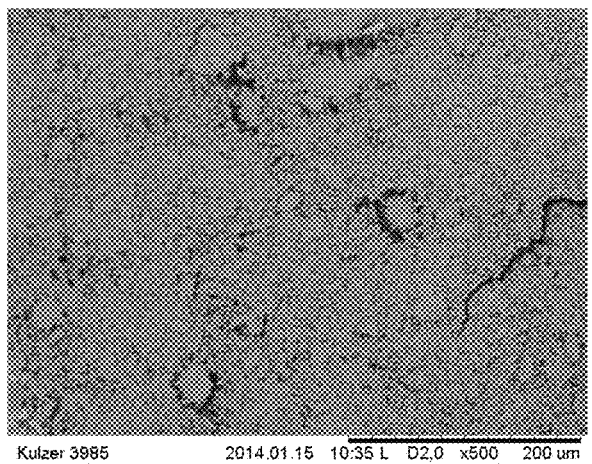
Figure 1D:
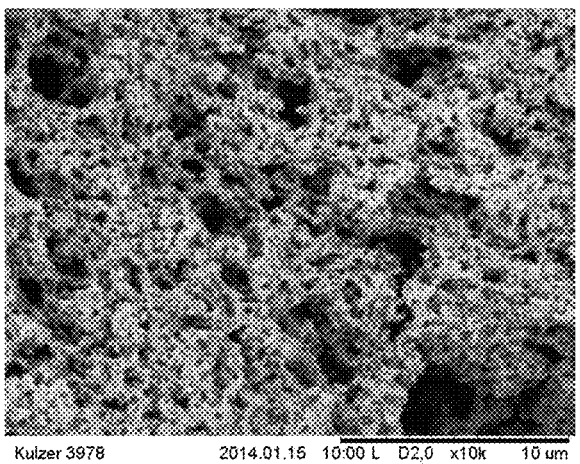

Producing the powder mixture (B) according to the invention: A mixture is produced from PMMA beads of different particle sizes (bead 1 homopolymer ($d_{50}$~40-50 μm) 60-70%, bead 2 ($d_{50}$~55-70 μm) 15%, bead 3 copolymer (d50~40-50 μm) 15%) with the addition of barbituric acid and colour pigments.

Producing the liquid/monomer mixture (A) according to the invention: A mixture is produced from methylmethacrylate, and another methacrylate-based multi-crosslinker with the addition of stabilizers and initiators (barbituric acid/copper-system). In addition, the urethane dimethacrylate according to the invention, as well as the core-shell particles according to the invention are being added.

Example according to the invention powder mixture and liquid mixture:

|  | Example 1 | Comparative Ex. 1 without core-shell and without urethane (meth)acrylate | Comparative Ex. 2 without core-shell and with urethane (meth)acrylate | Comparative Ex. 3 with core-shell and without urethane (meth)acrylate |
|---|---|---|---|---|
| Liquid |  |  |  |  |
| methylmethacrylate | 93.3 | 98.3 | 95.3 | 96.3 |
| 2-(4,6-diphenyl-1,3,5-triazine-2-yl)-5-((hexyl)oxy)-phenol | 0.3 | 0.3 | 0.3 | 0.3 |
| N-methyl-N,N-dioctyloctane-1-ammoniumchloride | 0.2 | 0.2 | 0.2 | 0.2 |
| solution of copper(II) chloride | 0.1 | 0.1 | 0.1 | 0.1 |
| N,N-Bis(2-hydroxyethyl)-p-toluidine | 0.1 | 0.1 | 0.1 | 0.1 |
| total | 94.00 | 99.00 | 96.00 | 97.00 |
| di-functional aliphatic urethane acrylate oligomer | 3.00 | — | 3.00 | — |
| tris(2-hydroxyethyl)-isocyanurate triacrylate | 1.00 | 1.00 | 1.00 | 1.00 |
| core-shell particles | 2.00 | — | — | 2.00 |
| total | 100.00 | 100.00 | 100.00 | 100.00 |
| Powder |  |  |  |  |
| PMMA/PMA $d_{50}$~40-45 μm | 67.5 | 67.5 | 67.5 | 67.5 |
| PMMA $d_{50}$~40-55 μm | 15.000 | 15.000 | 15.000 | 15.000 |
| cross-linked PMMA $d_{50}$~55-70 μm | 15.000 | 15.000 | 15.000 | 15.000 |
| phenylbenzylbarbituric acid | 2.5 | 2.5 | 2.5 | 2.5 |
| total | 100.000 | 100.000 | 100.000 | 100.000 |

TABLE 1

Comparison of the example according to the invention and the comparative examples
Physical properties (Norm ISO 20795-1)

|  | Example 1 | Comparative Ex. 1 | Comparative Ex. 2 | Comparative Ex. 3 |
|---|---|---|---|---|
| flexural strength [MPa] | >60 | 69.7 | 69.1 | 67.8 | 70.5 |
| E-modulus [MPa] | >1500 | 2365 | 2417 | 2374 | 2397 |
| fracture toughness [MPa m1/2] | >1.9 | 2.45 | 1.77 | 1.77 | 2.39 |
| total fracture work [J/m$^2$] | >900 | 1041.18 | 325.61 | 340.37 | 856.67 |
| transparency [delta %] (after 6 d/37° C. of storage in Ringer's solution) |  | −3.16 | −7.04 | −4.88 | −3.36 |

Production of test bodies, determination of colour values, determination of mechanical properties:

Colour test bodies: The following powder mixtures and monomer mixtures at a ratio of 10 g powder to:7 ml liquid are vigorously mixed and test bodies with dimensions of 30×30×3 mm are poured after the swelling phase (approximately 5 min at 23° C.) and polymerised in Palamat elite for 30 min at 55° C. and 2 bar pressure.

Test bodies for mechanical strength: The following powder mixtures and monomer mixtures at a ratio of 10 g powder:7 ml liquid are vigorously mixed and test bodies with dimensions of 100×100×5 mm are poured after the swelling phase (approximately 5 min at 23° C.) and polymerised in Palamat elite for 30 min at 55° C. and 2 bar pressure.

Subsequently, the test plates are sawed to the geometry stated in ISO 20795-1 and are polished.

Test bodies for mechanical tests are produced in steel moulds, test bodies for colorimetric tests are produced in duplicating gels.

To determine the transparency, the test bodies are stored for 5 days in Ringer's solution at 37° C., and the colour values and transparency are determined both before and after storage using 3 mm-plates. The measurements of table 1 are made according to DIN EN ISO 20795-1.

The monomer mixture according to the invention shows significantly improved fracture toughness over all comparative examples, increased transparency, as well as the least loss of transparency after storage in Ringer's solution (reduced tendency to whitening).

The invention claimed is:

1. Autopolymerisable two-component prosthetic base material comprising a mixture of the following components (A) and (B):
   (A) at least one liquid monomer component,
   (B) at least one powdered component,
   wherein
   the at least one liquid monomer component (A) comprises:
   (i) at least one initiator or one initiator system for autopolymerisation,
   (ii) core-shell particles modified by an elastic phase,
   (iii) at least one urethane dimethacrylate; and
   (iv) at least one polymerizable monomer;
   wherein (ii) core-shell particles modified by at least one elastic phase are present at 0.001 to 5% by weight, based on a total weight of component (A).

2. Prosthetic base material according to claim 1, wherein the distribution of the elastic phase of the modified core-shell particles is selected from possibilities a to d:
   a) elastic phase as core in solid outer shell (core-shell-particles);
   b) multiple elastic phases as cores in a solid matrix;
   c) core-shell particles from a) distributed in solid matrix, and
   d) solid core with elastic phase as outer shell.

3. Prosthetic base material according to claim 1, wherein the at least one powdered component (B) comprises:
   a) polymeric particles comprising polymers in the form of polymer powder comprising polyalkyl(meth)acrylates, optionally being crosslinked and being present as homopolymer or copolymer, whereby the polymers are based on at least one monomer comprising a (meth) acrylate group, selected from methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethyl methacrylate, hydroxypropylmethacrylate, a mixture comprising at least one of said (meth)acrylates and/or copolymers comprising one or at least two of the afore-mentioned monomers, polyamide particles, polyamide fibers, and optionally
   b) inorganic fillers comprising pyrogenic or precipitated silicas, dental glasses, zeolites, amorphous spherical fillers based on oxide or mixed oxide, glass fibres and/or carbon fibers, as well as mixtures comprising said powdered components a) and b).

4. Prosthetic base material according to claim 1, wherein the at least one powdered component (B) comprises polymethylmethacrylate (PMMA) beads as polymeric particles and/or splitter polymers, copolymers, comprising as comonomers, being polymerised into the copolymer, styrene, alpha-methylstyrene, vinyltoluene, substituted vinyltoluene, vinylhalogenide, vinylester, heterocyclic vinyl compounds, cyclopentene, (meth)acrylic acid ester, further acrylonitrile, maleic acid and maleic acid derivatives, fumaric acid and fumaric acid derivatives, acrylic acid, methacrylic acid, acryl(meth)acrylates, as well as, optionally, mixtures of said comonomers.

5. Prosthetic base material according to claim 1, wherein the elastic phase is selected from poly-(n-butyl acrylates) (PBA), butadiene-styrene copolymers, nitrile-butadiene copolymers, silicon rubber (graft copolymers), polyurethane polymers, polyolefin-based polyurethanes (polybutadiene-based polyurethanes), polydimethylsiloxane-modified polyurethanes, epoxy-functionalised elastic phases.

6. Prosthetic base material according to claim 1, wherein the solid shell, the solid core and/or the solid matrix are selected from (meth)acrylate polymers, polystyrene, epoxy-functionalised shell, metal oxide particles less than 100 nm as core, as well as homo-condensates or co-condensates of the afore-mentioned polymers.

7. Prosthetic base material according to claim 1, wherein the at least one liquid monomer component (A) comprises at least one monomer or a mixture of monomers selected from:
   a) methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, benzyl-, furfuryl- or phenyl(meth)acrylate, a mixture comprising at least one of said (meth)acrylates and/or copolymers comprising one or at least two of the afore-mentioned monomers, and/or
   b) two- and/or multi-crosslinking agents comprising 1,4-butandiol dimethacrylate (1,4-BDMA) or pentaerythritol tetraacrylate, bis-GMA monomer (bisphenol-A-glycidylmethacrylate, triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra(meth)acrylate, as well as butanediol di(meth)acrylate, ethylene glycol di(meth)acrylate, polyethylene glycol di(meth)acrylate, ethoxylated/propoxylated bisphenol-A-di(meth)acrylate, a mixture comprising at least one of said (meth)acrylates and/or copolymers comprising one or at least two of the afore-mentioned monomers.

8. Prosthetic base material according to claim 1, wherein at least some of the core-shell particles are present as aggregates of primary particles and the primary particles of the core-shell particles have diameters from 500 nm to 10 nm.

9. Prosthetic base material according to claim 1, which additionally comprises one or more substances from the group consisting of fillers, pigments, stabilizers, regulators, antimicrobial additives, UV-absorbing agents, thixotroping agents, catalysts and crosslinkers.

10. Prosthetic base material according to claim 1, which additionally comprises at least one initiator or at least one initiator system for autopolymerisation, which are present in (A) and (B).

11. Prosthetic base material according to claim 1, wherein the at least one initiator or the at least one initiator system for autopolymerisation comprises
    a) at least one initiator, and optionally
    b) at least one activator, or
    c) at least one initiator system selected from redox system.

12. Prosthetic base material according to claim 1, comprising
    (ii) core-shell particles modified by at least one elastic phase of 0.001 to 10% by weight, based on the total composition of component (A), and
    (iii) at least one urethane dimethacrylate of 0.001 to 20% by weight, based on the total composition of component (A).

13. Method for producing a polymerized prosthetic base material, said comprising the following steps: (a) providing a prosthetic base material according to claim 1 and (b) polymerizing the prosthetic base material.

14. Method according to claim 13, wherein component (A) and component (B) are present in the prosthetic base material at a weight ratio of (A):(B) ranging from 1:50 to 50:1.

15. Method according to claim 13, which comprises before step (b) introducing the prosthetic base material into a negative form of at least one dental prosthetic molded body.

16. Polymerised prosthetic base material obtainable by a method according to claim 13.

17. Polymerised prosthetic base material according to claim 16, which has a fracture toughness of $\geq 1.9$ Mpa·m$^{1/2}$ and a total fracture work of $\geq 900$ J/m$^2$.

18. Kit comprising an autopolymerisable prosthetic base material according to claim 1, whereby the kit comprises separated components (A) and (B).

19. An autopolymerisable two-component prosthetic base material comprising a mixture of the following components (A) and (B):
    (A) at least one liquid component, and
    (B) at least one powdered component,
    wherein
    the at least one liquid component (A) comprises:
    (i) at least one initiator or one initiator system for autopolymerisation,
    (ii) 0.001 to 5% by weight, based on a total weight of all liquid components, of formerly aggregated core-shell particles that have been degraded by suspending into core-shell primary particles, the core-shell primary particles being modified by an elastic phase,
    (iii) at least one urethane dimethacrylate, and
    (iv) at least one polymerizable monomer.

20. A method for producing a polymerised prosthetic base material, said method comprising polymerizing the autopolymerisable two-component prosthetic base material according to claim 19.

21. Polymerised prosthetic base material obtained by the method according to claim 20.

* * * * *